(12) United States Patent (10) Patent No.: US 8,707,378 B2
Nambakkam et al. (45) Date of Patent: Apr. 22, 2014

(54) CATALOG AND USER APPLICATION FOR A VIDEO PROVISIONING SYSTEM

(75) Inventors: Sampath K. Nambakkam, Irving, TX (US); Nagaviswas Ventrapragada, Coppell, TX (US)

(73) Assignee: Verizon Patent and Licensing Inc., Basking Ridge, NJ (US)

( * ) Notice: Subject to any disclaimer, the term of this patent is extended or adjusted under 35 U.S.C. 154(b) by 47 days.

(21) Appl. No.: 13/196,587

(22) Filed: Aug. 2, 2011

(65) Prior Publication Data

US 2012/0079512 A1 Mar. 29, 2012

Related U.S. Application Data

(60) Provisional application No. 61/387,939, filed on Sep. 29, 2010.

(51) Int. Cl.
*H04N 7/173* (2011.01)
*H04N 7/16* (2011.01)
*G06F 7/00* (2006.01)
*G06F 17/00* (2006.01)

(52) U.S. Cl.
USPC ............ 725/115; 725/91; 707/610; 707/624

(58) Field of Classification Search
USPC ............... 725/54, 92, 91, 115; 707/610, 624
See application file for complete search history.

(56) References Cited

U.S. PATENT DOCUMENTS

| | | | | |
|---|---|---|---|---|
| 5,543,851 | A * | 8/1996 | Chang | 348/468 |
| 7,904,678 | B1 * | 3/2011 | Karr et al. | 711/162 |
| 8,019,722 | B2 * | 9/2011 | Linkert et al. | 707/617 |
| 8,261,307 | B1 * | 9/2012 | Islam et al. | 725/62 |
| 2007/0044133 | A1 * | 2/2007 | Hodecker | 725/117 |
| 2008/0086747 | A1 * | 4/2008 | Rasanen et al. | 725/46 |
| 2008/0235104 | A1 * | 9/2008 | Chow et al. | 705/26 |
| 2008/0276278 | A1 * | 11/2008 | Krieger et al. | 725/40 |
| 2008/0320543 | A1 * | 12/2008 | Wang et al. | 725/131 |
| 2009/0319370 | A1 * | 12/2009 | Jain | 705/14.54 |
| 2010/0106684 | A1 * | 4/2010 | Pizzo et al. | 707/610 |
| 2010/0146567 | A1 * | 6/2010 | Mehta et al. | 725/91 |
| 2010/0153334 | A1 * | 6/2010 | Takemura et al. | 707/610 |
| 2010/0161716 | A1 * | 6/2010 | Kajos et al. | 709/203 |
| 2010/0180308 | A1 * | 7/2010 | Howcroft et al. | 725/53 |
| 2010/0251280 | A1 * | 9/2010 | Sofos et al. | 725/14 |
| 2011/0067049 | A1 * | 3/2011 | Piepenbrink et al. | 725/30 |
| 2011/0119696 | A1 * | 5/2011 | Piepenbrink et al. | 725/23 |
| 2011/0145187 | A1 * | 6/2011 | Himmelsbach et al. | 707/610 |
| 2011/0161995 | A1 * | 6/2011 | Paul et al. | 725/5 |
| 2011/0219229 | A1 * | 9/2011 | Cholas et al. | 713/168 |
| 2011/0282949 | A1 * | 11/2011 | Rivkin | 709/206 |
| 2011/0306368 | A1 * | 12/2011 | McCarthy | 455/466 |
| 2012/0078703 | A1 * | 3/2012 | Berger et al. | 705/14.27 |
| 2012/0079606 | A1 * | 3/2012 | Evans et al. | 726/28 |
| 2012/0157043 | A1 * | 6/2012 | LaJoie et al. | 455/407 |
| 2012/0297084 | A1 * | 11/2012 | Gordon | 709/233 |

* cited by examiner

*Primary Examiner* — James R Sheleheda

(57) ABSTRACT

A method performed by a video provisioning system may include receiving metadata associated with a video asset; storing the metadata in a catalog of video assets available through the video provisioning system; publishing information from the stored metadata to a first device associated with a video assets store front for set top boxes; and publishing information from the stored metadata to a second device associated with a video assets store front for devices other than set top boxes. A method may further include registering a user device with a user profile; identifying a media manager application for the user device that is configured to play video assets available via the video provisioning system on the user device; providing the media manager application to the user device; and synchronizing settings associated with the media manager application with settings associated with another user device registered with the user profile.

25 Claims, 11 Drawing Sheets

CATALOG AND USER APPLICATION FOR A VIDEO PROVISIONING SYSTEM

REFERENCE TO RELATED APPLICATION

This application claims priority to U.S. Provisional Patent Application No. 61/387,939, filed Sep. 29, 2010, the entire contents of the provisional application being incorporated herein by reference.

BACKGROUND INFORMATION

Video content may be available from many sources and may be delivered to users through a variety of methods. For example, video content may be available from commercial broadcasting television networks (e.g., ABC, CBS, NBC, FOX, etc.) via free broadcast; from a cable television service (e.g., CNN, TNT, TBS, etc.) for a periodic subscription fee; from a satellite television service (e.g. DirectTV, Dish Network, etc.) for a periodic subscription fee; from a pay-per-view service; from an on-demand video service; from a over-the-top (OTT) content providers on the Internet (e.g., Hulu, Veoh, Jaman, YouTube, etc.); and/or from any other commercial supplier (e.g., iTunes, Netflix, Blockbuster, etc.). Video content may be delivered to users, for example, via a set top box, a computer device, a wireless mobile device. Managing a catalog of video assets, or managing user applications associated with the video assets, may be challenging.

DETAILED DESCRIPTION OF PREFERRED EMBODIMENTS

Figure 1:
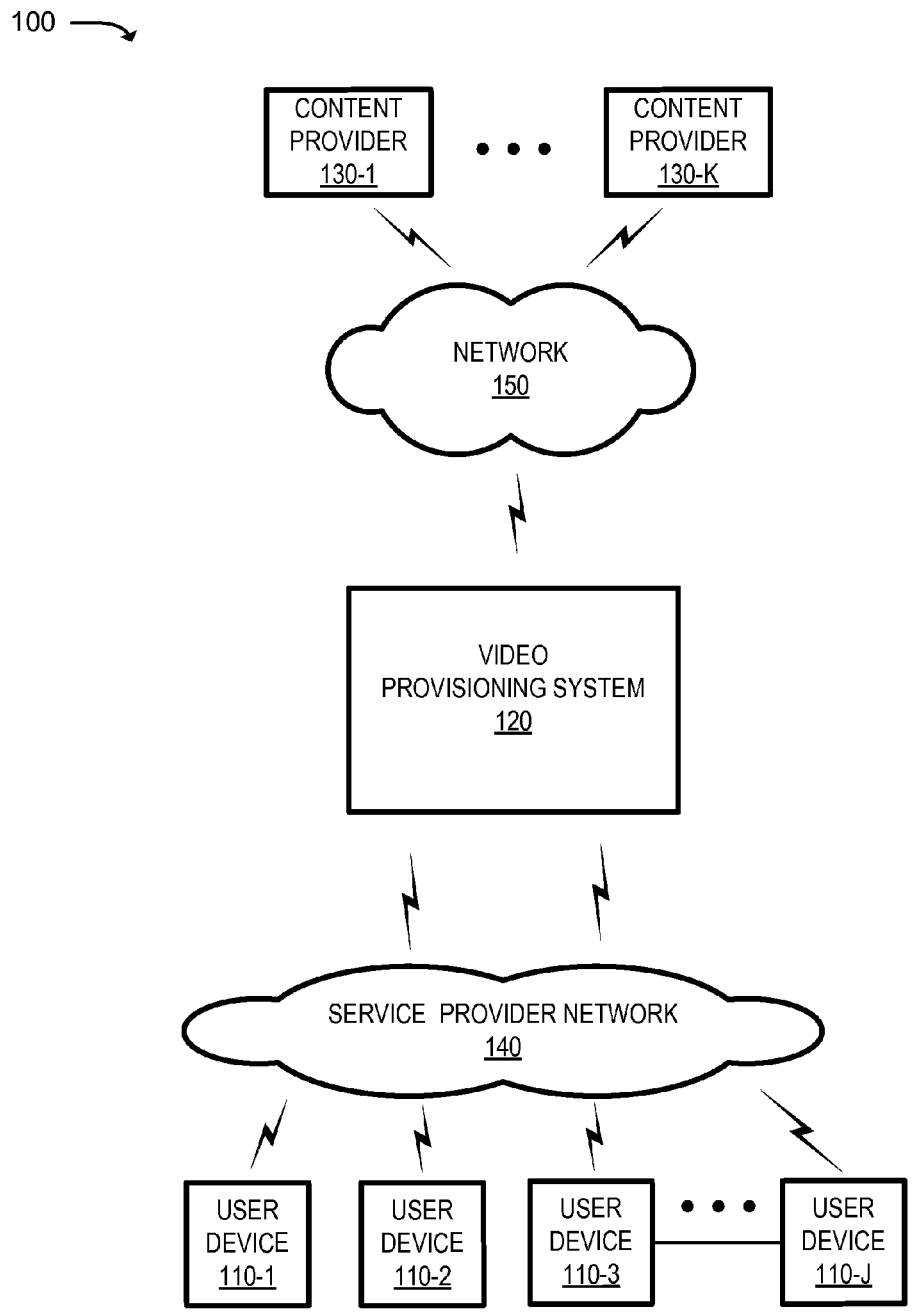
FIG. 1 is a diagram illustrating an example environment according to an implementation described herein.

The following detailed description refers to the accompanying drawings. The same reference numbers in different drawings identify the same or similar elements.

An implementation described herein may relate to a catalog and a user application for a video provisioning system (VPS). The VPS may enable the video content to be provisioned with a uniform price, availability, and/or accessibility, regardless of a type of network via which the video content is being provisioned and/or a type of user device for which the video content is obtained. Thus, video content may be provisioned for computer devices (e.g., desktop computers, laptop computers, and tablet computers), wireless handheld devices (e.g., mobile phones, smart phones, personal digital assistants (PDAs), and tablet computers), and set top boxes.

The video content may be provisioned to the computer devices, wireless handheld devices, and/or set top boxes via a federated network environment that includes a number of different types of networks, such as, for example, a wired network, a wireless network, a broadband network, a cellular telephone network, a television network, etc., and/or some combination thereof. For example, video content may be provisioned to a set top box via a managed television network that transmits the video content (e.g., via a video stream) to the set top box. The managed television network may stream the video content using, for example, a conditional access encryption technique. The managed television network may provide the video content to the set top box in a manner that conforms to a particular quality of service (QoS) level, data rate, etc.

In another example, the video content may be provisioned to a computer device, associated with a user of the set top box, via a broadband network (e.g., via progressive download, adaptive bit rate streaming, etc.), such as, for example, the Internet. The video content, in this example, may be encrypted using another encryption technique (e.g., based on digital rights management and/or some other technique) and/or another QoS level (e.g., best efforts and/or some other QoS level) associated with the broadband network. In yet another example, the video content may be provisioned to a wireless handheld device, associated with the user, via a wireless network (e.g., via progressive download, adaptive bit rate streaming, etc.). The video content, in this example, may be encrypted using a further encryption technique (e.g., based on digital rights management and/or some other technique) and/or a further QoS level (e.g., best efforts or some other QoS level) associated with the wireless network and/or a type of wireless handheld device.

The term video content, as used herein, may include one or more video assets, metadata associated with the video assets, and/or information associated with digital rights management (DRM) that corresponds to the video assets. The video assets may include Video On-Demand (VOD) video content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. The information associated with the DRM may include license information that identifies terms and/or conditions for handling, promoting, distributing, and/or using the video assets and/or enables video assets to be encrypted and/or decrypted (e.g., based on keys associated with the license information).

The metadata may enable the video assets to be identified, managed, merchandized, and/or distributed to a user device. The metadata may, for example, include an identifier associated with a video asset (e.g., a number, a name, a title, etc.); a genre of the video asset (e.g., horror, comedy, adult, etc.); a category of the video asset (e.g., VOD asset, a PPV asset, etc.); a text description of the video asset; and/or information associated with artists associated with the video asset (e.g., names of actors, directors, producers, etc.). The metadata may also, or alternatively, include information associated with a type of video asset (e.g., a movie, music video, a game, etc.); a rating associated with the video asset (e.g., general audience (G), parental guidance (PG), PG-13, restricted (R), mature audience (MA), etc.); user reviews associated with the video asset; a price associated with the video asset (e.g., a sale price, a rental price per day, a pay-per-view price, etc.); and/or an availability period associated with the video asset (e.g., release dates, restriction periods, blackout periods, etc.). The metadata may also, or alternatively, include information associated with a storage location (e.g., a uniform resource locator (URL)) corresponding to the video asset; a format associated with the video asset (e.g., a resolution level, compression/decompression (CODEC) information, a screen size, a frame size, a frame refresh rate, a bit rate, etc.); and/or types of user devices supported by each format, etc.

An implementation described herein may relate to a catalog for the VPS. A catalog server device may receive metadata associated with video assets and may process and store the metadata in a catalog of video assets. The catalog server device may, for example, generate index information for a video asset, generate a price structure for the video asset, generate bundle information for the video asset, generate availability information for the video asset, and/or associate digital rights management (DRM) information with the video asset.

The catalog server device may further associate, with the video asset, a storage location of a first copy of the video asset that has been formatted for a set top box and may associate, with the video asset, a storage location of a second copy of the video asset that has been formatted for a device different from a set top box (e.g., a personal computer, a mobile communication device, a gaming console, etc.).

The catalog server device may further publish information about the video asset to a first device that is associated with a first store front for browsing and purchasing video assets through a set top box and may publish information about the video asset to a second device that is associated with a second store front for browsing and purchasing video assets through a device different from a set top box (e.g., a personal computer, a mobile communication device, a gaming console, etc.).

An implementation described herein may further relate to synchronizing a first catalog of video assets associated with a first store front accessible through a set top box and a second catalog of video assets associated with a second store front accessible through devices different from a set top box. The catalog synchronization may be performed by a video content management server that ingests video assets, and metadata associated with the video assets, from content providers and provides the ingested information to the catalogs.

An implementation described herein may relate to providing a user application to a user device other than a set top box. The user application, referred to herein as a media manager application, may enable the user device to access a store front of the VPS to browse, purchase video assets available via the VPS, and consume (i.e., view or play) purchased video assets on the user device. A user may be able to register different types of user devices with VPS and the VPS may provide a media manager application for each type of user device. The VPS may register a user device, identify a particular media manager application for the device, and provide the identified media manager application to the registered device.

Furthermore, the VPS may synchronize settings associated with the media manager application based on settings associated with another user device registered with the VPS under the same user profile. Moreover, the VPS may synchronize downloaded video assets by identifying video assets that have been downloaded to another user device and downloading the identified video assets to the registered user device.

FIG. 1 is a diagram of an example environment in which the systems and/or methods, described herein, may be implemented. As shown in FIG. 1, environment 100 may include a group of user devices 110-1, . . . , 110-J (where J≥1) (referred to herein collectively as "user devices 110" and individually as "user device 110"), a video provisioning system (VPS) 120, a group of content providers 130-1, . . . , 130-K (where K≥1) (referred to herein collectively as "content providers 130" and individually as "content provider 130"), a service provider network 140, and a network 150. Devices, systems, and/or networks of environment 100 may interconnect via wired connections, wireless connections, or a combination of wired and wireless connections.

User device 110 may include a computation or communication device that is capable of communicating with service provider network 140. For example, user device 110 may include a radiotelephone, a personal communications system (PCS) terminal (e.g., that may combine a cellular radiotelephone with data processing and data communications capabilities), a personal digital assistant (PDA) (e.g., that can include a radiotelephone, a pager, Internet/intranet access, etc.), a laptop computer, a tablet computer, a set top box, a digital video recorder (DVR), a personal gaming system, a smart phone, and/or another type of computation or communication device.

User device 110 may communicate with VPS 120 and/or perform certain operations to obtain a video asset from VPS 120. For example, user device 110 may access a portal (e.g., a website, a user interface, an interactive program guide (IPG), an interactive media guide (IMG), etc.) associated with VPS 120, to browse, search, select, and/or obtain a video asset.

VPS 120 may include one or more devices that gather, process, search, store, and/or provide information in a manner similar to that described herein. VPS 120 may be capable of communicating with content providers 130 via network 150 and/or user devices 110 via service provider network 140. VPS 120 may provide a video provisioning service to user devices 110.

VPS 120 may, for example, perform operations associated with video content ingestion, processing, and/or distribution for one or more types of user devices 110, associated with a user, within environment 100. VPS 120 may communicate with one or more content providers 130 to acquire video content. VPS 120 may connect to a collection of various types user devices 110 associated with a user, such as, for example, a set top box, a computer device, a wireless handset device (e.g., a smart phone, a personal digital assistant (PDA), etc.), and/or other types of user devices 110. VPS 120 may connect to the set top box via a television service provider network 140 (e.g., a cable television network, a satellite television network, a fiber optic television network, or some combination thereof). VPS 120 may connect to the computer device via a broad band service provider network 140 (e.g., via the Internet). VPS 120 may connect to the wireless handset device via a wireless service provider network 140. VPS 120 may perform an ingestion operation on the acquired video content. VPS 120 may process and/or publish the ingested video content in a manner that allows the video content to be offered and/or distributed to the different types of user devices 110.

Content provider 130 may include any type or form of content provider. For example, content provider 130 may include free television broadcast providers (e.g., local broadcast providers, such as NBC, CBS, ABC, and/or Fox), for-pay television broadcast providers (e.g., TNT, ESPN, HBO, Cinemax, CNN, etc.), and/or Internet-based content providers (e.g., Youtube, Vimeo, Netflix, Hulu, Veoh, etc.) that stream content from web sites and/or permit content to be downloaded (e.g., via progressive download, etc.). Content provider 130 may include on-demand content providers (e.g., video on demand (VOD), pay per view (PPV), etc.). A media stream, as used herein, may refer to a stream of content that includes video content (e.g., a video stream), audio content (e.g., an audio stream), and/or textual content (e.g., a textual stream).

The term video asset, as used herein, may include VOD content, pay-per-view (PPV) video content, rented video content, free television content (e.g., from free television broadcasters, etc.), paid for television content (e.g., from pay television content providers), on-line video content (e.g., on-line television programs, movies, videos, etc.), advertising, games, music videos, promotional information (e.g., such as previews, trailers, etc.), etc. A video asset may be stored in one or more video files that contain video information that can be played on a user device.

Service provider network 140 may include one or more wired and/or wireless networks via which user devices 110 communicate with and/or receive video content from VPS 120. For example, service provider network 140 may include a cellular network, the Public Land Mobile Network (PLMN), a second generation (2G) network, a third generation (3G) network, a fourth generation (4G) network (e.g., a long term evolution (LTE) network), a fifth generation (5G) network, and/or another network. Additionally, or alternatively, service provider network 140 may include a code division multiple access (CDMA) network, a global system for mobile communications (GSM) network, a general packet radio services (GPRS) network, or a combination of CDMA, GSM, and/or GPRS networks. Additionally, or alternatively, service provider network 140 may include a wide area network (WAN), a metropolitan area network (MAN), an ad hoc network, an intranet, a fiber optic-based network (e.g., a fiber optic service (FiOS) network), a television network, and/or a combination of these or other types of networks.

Network 150 may include one or more wired and/or wireless networks. For example, network 150 may include a cellular network, the PLMN, a 2G network, a 3G network, a 4G network (e.g., an LTE network), a 5G network, and/or another network. Additionally, or alternatively, network 150 may include a WAN, a MAN, a telephone network (e.g., the Public Switched Telephone Network (PSTN)), an ad hoc network, an intranet, the Internet, a fiber optic-based network, and/or a combination of these or other types of networks.

Although FIG. 1 shows example components of environment 100, in other implementations, environment 100 may include fewer components, different components, differently arranged components, or additional components than depicted in FIG. 1. Additionally or alternatively, one or more components of environment 100 may perform functions described as being performed by one or more other components of environment 100.

Figure 2:
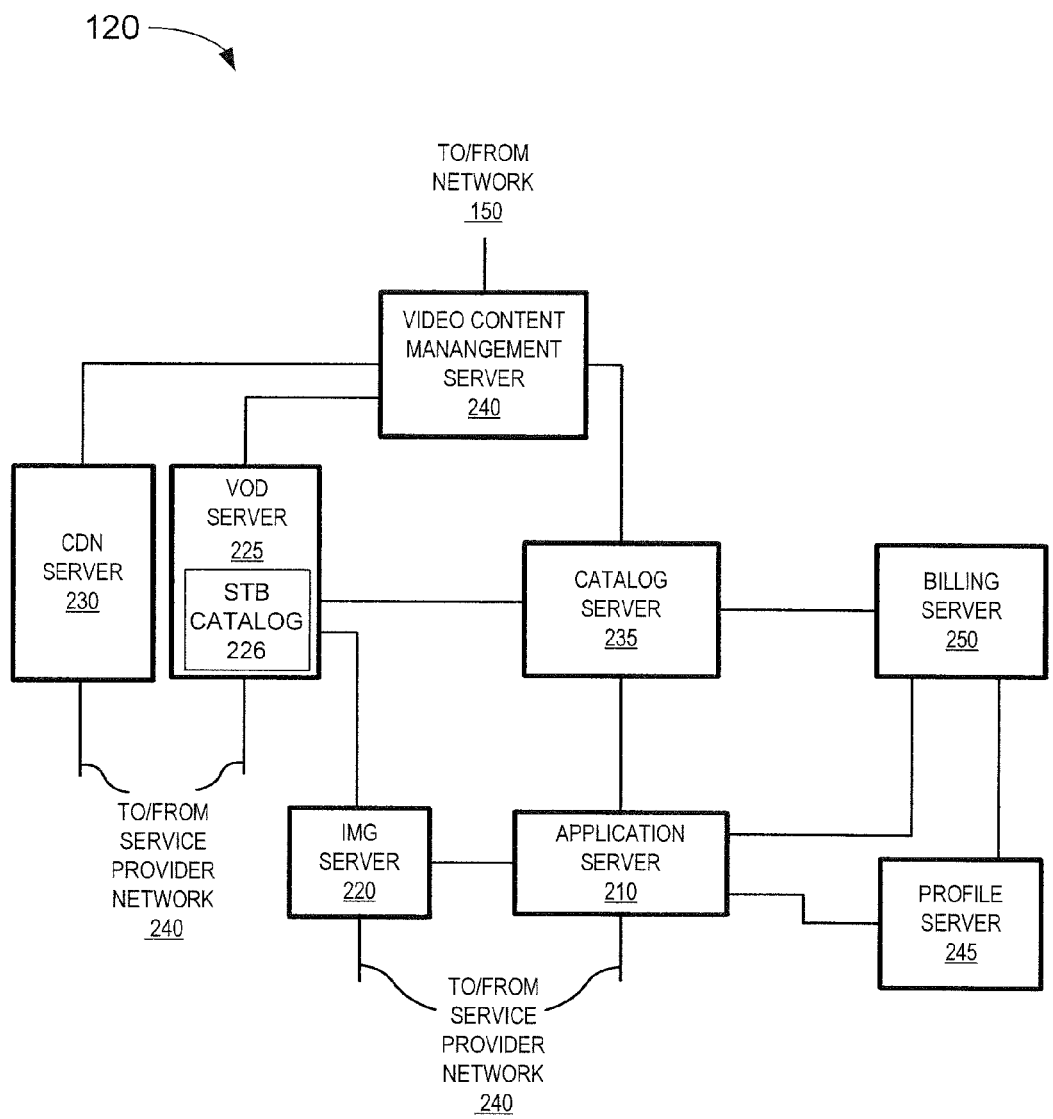
FIG. 2 is a diagram illustrating example components associated with the video provisioning system of FIG. 1.

FIG. 2 is a diagram of example devices associated with VPS 120. As shown in FIG. 2, VPS 120 may include an application server 210, an interactive media guide (IMG) server 220, a video on-demand (VOD) server 225, a content delivery network (CDN) server 230, a catalog server 235, a video content management (VCM) server 240, a profile server 245, and a billing server 250.

In the description below, VOD server 225 is described as provisioning video services for a type of user device 110 (i.e., a set top box) and CDN server 230 is described as provisioning video services for another type of user device 110 (i.e., a computer device, a wireless handset device, etc.) for explanatory purposes. In another implementation, the video services may be provisioned for the set top box and/or the other types of user devices 110 in a number of ways. For example, VOD server 225 and/or CDN server 230 may be combined into a single device that provisions the video services for each type of user device 110. In another example, the video services may be provisioned, for each type of user device 110, by another device and/or network instead of, or in combination with, VOD server 225 and/or CDN server 230. Additionally, IMG server 220 is described as providing a store front portal (i.e., via an IMG), that can be accessed by the set top box, and application server 210 is described as providing another store front portal (e.g., via a web page, a user interface, an interactive program guide, etc.), that can be accessed by the other types of user devices 110, for explanatory purposes. In another implementation, the store front portal may be provisioned for the set top box and/or the other types of user devices 110 in a number of ways. For example, IMG server 220 and/or application server 210 may be combined into a single device that provisions the store front portal for each type of user device 110. In another example, the store front portal may be provisioned, for each type of user device 110, by another device and/or network instead of, or in combination with, IMG server 220 and/or application server 210. Thus, the examples below are provided for explanatory purposes only.

Application server 210 may include one or more server devices, or other types of computation or communication devices, that gather, process, search, store, and/or provide information in a manner similar to that described herein. Application server 210 may receive metadata that has been published by catalog server 235. The metadata may be associated with video assets that are to be made available and/or offered (e.g., for sale, rent, subscription, etc.) to user devices 110. Application server 210 may host a portal (e.g., a VPS store front), such as a private website (e.g., for subscribing user devices 110), a public website (e.g., for non-subscribing user devices 110), a user interface (UI) (e.g., that is accessible by wireless mobile handset-type user devices 110, etc.), an interactive program guide (e.g., an IMG for set top box-type user devices 110) and/or other types of user interfaces. The portal may enable single sign-on (SSO) portal access, to a user of one or more user devices 110, based on the same login credentials (e.g., username, password, personal identification number (PIN), etc.). Application server 210 may publish all or a portion of the metadata to the portal that permits any of user devices 110 to browse, perform searches, process payment, etc. for video assets based on the metadata that is published to the portal.

Application server 210 may perform a session management operation that authenticates user device 110 when user device 110 attempts to access the store front portal. Application server 210 may retrieve, from profile server 245, information relating to a profile associated with a user of one or more user devices 110. Application server 210 may obtain, from the information associated with the profile, information associated with a type of user device 110, a video format (e.g., screen size, bit rate, frame size, a frame reset rate, etc.) supported by user device 110, parental controls specified by the user, a transaction history associated with the user, a bookmark associated with a video asset, etc.

Application server 210 may permit user device 110 to browse and/or search video assets provided by VPS 120. Application server 210 may permit user device 110 to preview a trailer associated with a video asset and/or to select a video asset via the portal. Application server 210 may store information associated with the selected video asset in a logical shopping cart and/or electronic invoice. Application server 210 may recommend other video assets based on information associated with the transaction history and/or the parental controls. Application server 210 may perform an electronic transaction that permits user device 110 to purchase, rent, etc. a selected video asset (e.g., that was stored in the logical shopping cart), purchase a subscription for one or more video assets, bundles, etc. Application server 210 may, in one example, process payment information obtained from the information associated with the profile. Application server 210 may, in another example, send a notification, to billing server 250, that includes information associated with the transaction and which enables billing server 250 to include a cost of the transaction in an account associated with user device 110.

Application server 210 may send a notification to catalog server 235 that identifies the selected video content. The notification may include an indication of the type of user device 110 and/or information associated with the video format that user device 110 supports. Application server 210 may send an indication, to profile server 245, that the transaction associated with the selected video content was executed. The indication may enable other user devices 110, associated with the user, to obtain a copy of the selected video (e.g., in a video format supported by the other user devices 110) content at no additional cost to the user.

Application server 210 may register user device 110 with a user profile. For example, when a user wants to add a new user device 110 (e.g., a personal computer, mobile communication device, gaming console, etc.) to the user's profile, the user may use the new user device 110 to access the public store front associated with application server 210, may log in with a username and password, and may request to add the new user device 110 to the user's profile. Application server 210 may instruct profile server 245 to add the new user device 110 to the user's profile.

Application server 210 may identify a media manager application for the newly registered user device 110. Each particular type of user device 110 may be associated with a particular media manager application. Application server 210 may select an appropriate media manager application for the newly registered user device 110 and may provide the selected media manager application to the newly registered user device 110. Application server 210 may synchronize settings associated with the selected media manager application with settings associated with another registered user device 110. Application server 210 may further identify video assets downloaded to the other registered user device 110 and may download the identified video assets to the newly registered user device 110.

IMG server 220 may include one or more server devices, or other types of computation or communication devices, that gather, process, search, store, and/or provide information in a manner similar to that described herein. IMG server 220 may, for example, process metadata, that has been published by catalog server 235 and/or VOD server 225, in a manner similar to that described above (e.g., with respect to application server 210). The metadata may be associated with video content that may be obtained by a particular type of user device 110, such as a set top box user device 110.

IMG server 220 may publish all or a portion of the metadata to an IMG UI that the set top box user device 110, associated with the user, may render for display on a video display device. IMG server 220 may permit the set top box user device 110 to access information associated with video assets, stored by VOD server 225, and access the actual video assets. IMG server 220 may, in another example implementation, communicate with application server 210, which may permit the set top box user device 110 to access the metadata associated video assets that are stored in CDN server 230.

IMG server 220 may store information associated with a transaction history that corresponds to a set top box user device 110. The transaction history may include information regarding prior transactions (e.g., purchases, rentals, subscriptions, etc.), associated with one or more video assets, by set top box user device 110. The transaction history may also identify a period of time during which a rental period or subscription period, for a video asset, is valid. Application server 210 may, in another example, transmit information, associated with the transaction history, to profile server 245, to be stored in a user profile associated with a user of user device 110.

VOD server 225 may include one or more server devices, or other types of computation or communication devices, that gather, process, search, store, and/or provide information in a manner similar to that described herein. VOD server 225 may, for example, perform operations to receive, store, process, and/or distribute video content in a format that is supported by set top box user devices 110.

VOD server 225 may receive published video assets and/or metadata from VCM server 240. VOD server 225 may store the published video assets in a memory associated with VOD server 225. VOD server 225 may include set top box (STB) catalog 226 that includes metadata associated with video assets received from VCM server 240. VOD server 225 may publish a portion of the metadata stored in STB catalog 226, associated with video assets (e.g., that are available for release and/or not subject to a blackout, etc.), to IMG server 220 that enables STB catalog 226 to be accessed, via IMG server 220, by set top box user devices 110. Thus, STB catalog 226 may be accessible through a set top box user device 110 via a store front of IMG server 220.

VOD server 225 may respond to requests for selected video assets. VOD server 225 may receive, from IMG server 220, an indication that a set top box user device 110 has selected a video asset from STB catalog 226 via IMG server 220. VOD server 225 may, in response to the indication, forward information associated with the selected video asset, such as, for example, an identifier associated with the selected video asset (e.g., a title asset identifier), information associated with content provider 130 (e.g., a provider identifier (PID)) from which the selected video asset was obtained, etc., to the set top box user device 110 via IMG server 220. VOD server 225 may receive, from the set top box user device 110, a request for the selected video asset and may transmit (e.g., via streaming video) the selected video asset to the set top box user device 110. The request may include the information associated with the selected video asset, the information associated with content provider 130, etc. The selected video asset may be encrypted (e.g., based on CAS-based encryption techniques) as the VOD server 225 is streaming the selected video asset to the set top box. The selected asset may be transmitted to the set top box in a manner that conforms to a particular QoS.

CDN server 230 may include one or more server devices, or other types of computation or communication devices, that gather, process, search, store, and/or provide information in a manner similar to that described herein. CDN server 230 may, for example, perform operations to receive, store, process, and/or distribute video content in a format that is supported by one or more types of user devices 110 (e.g., a computer device, a wireless mobile device, a gaming device, etc.) other than, or in addition to, a set top box user device 210. CDN server 230 may actually represent a content delivery network that includes multiple routing and/or storage devices.

CDN server 230 may receive published video assets in multiple video formats from VCM server 240. CDN server 230 may store the published video assets in a memory associated with CDN server 230. CDN server 230 may identify a respective storage location and/or URL for each format of each video asset that are stored within the memory and may send information associated with the storage locations and/or the URLs to catalog server 235.

CDN server 230 may respond to requests for selected video assets. CDN server 230 may receive, from user device 110, a request for a video asset based on a URL associated with the request. CDN server 230 may retrieve the video asset that is based on a particular video format that corresponds to the URL and may transmit the retrieved video asset to user device 110. CDN server 230 may encrypt the video asset (e.g., based on DRM-based encryption techniques) prior to transmitting the video asset to user device 110. The selected asset may be transmitted (e.g., based on a progressive download protocol, adaptive bit rate streaming protocol, and/or some other protocol) to user device 110 in a manner that conforms to another QoS (e.g., best efforts).

Catalog server 235 may include one or more server devices, or other types of computation or communication devices, that gather, process, search, store, and/or provide information in a manner similar to that described herein. Catalog server 235 may, for example, receive, from VCM server 240, published metadata associated with video content that has been published to VOD server 225 and/or CDN server 230. Catalog server 235 may process and/or package the metadata in order to merchandize the video content to which the metadata corresponds.

Catalog server 235 may, for example, obtain metadata for a video asset that includes, for the video asset, an identifier (e.g., a title, etc.), a description, a genre, casting information (e.g., actors, directors, producer, etc.), ratings, reviews, etc. Catalog server 235 may generate index information for the video asset. Catalog server 235 may merchandize the video asset by generating a price structure for the video asset that includes one or more prices. The prices may include a rental price (e.g., a price per single viewing, a price per day, per week, etc.), a sale price, a subscription price, etc. Catalog server 235 may associate the metadata, for the video asset, with other metadata, for other video assets, to create a service bundle (e.g., that includes the video asset and one or more other video assets and/or services) and may associate another price for the sale, rental, subscription, etc. of the service bundle.

Catalog server 235 may identify, from the metadata, information associated with the availability of the video asset based on a date on which the video asset is released, blacked out, etc. Catalog server 235 may publish the metadata, associated with the merchandized video assets, to the store front portal associated with application server 210. Catalog server 235 may not publish metadata associated with video assets that are identified as not yet being available. Catalog server 235 may publish other metadata associated with service bundles, promotions, recommendations, etc. to the store front portal.

Catalog server 235 may associate information associated with DRM with the metadata associated with the merchandized assets. Catalog server 235 may store the metadata for the video asset in a memory associated with catalog server 235. Catalog server 235 may include, with the metadata, a URL associated with a location at which the video asset is stored within CDN server 230.

VCM server 240 may include one or more server devices, or other types of computation or communication devices, that gather, process, search, store, and/or provide information in a manner similar to that described herein. VCM server 240 may, for example, communicate with content providers 130 to ingest video content to be processed by VPS 120. VCM server 240 may ingest high quality video content (e.g., associated with a resolution level and/or bit rate that is greater than a threshold). The video content may include one or more video assets, metadata associated with the video assets, and/or information associated with DRM that corresponds to the video assets. VCM server 240 may process the metadata to ensure that the metadata is supported by the different types of user devices 110.

VCM server 240 may publish the processed metadata to catalog server 235. In one example, catalog server 235 may process the metadata, received from VCM server 240, and provide the metadata to STB catalog 226. In another example, VCM server 240 may publish the processed metadata to STB catalog 226 and STB catalog 226 may process and store the metadata instead of receiving processed metadata from catalog server 235.

VCM server 240 may synchronize catalog server 235 and STB catalog 226. For example, VCM server 240 may obtain first metadata stored in catalog server 235, may obtain second metadata stored in STB catalog 226, may identify metadata that is missing from either catalog server 235 or STB catalog 226 based on the obtained metadata, and may provide the identified metadata to the catalog that is missing the identified metadata.

Profile server 245 may include one or more server devices, or other types of computation or communication devices, that gather, process, search, store, and/or provide information in a manner similar to that described herein. Profile server 245 may, for example, store information associated with a profile that includes information regarding the user and each user device 110 with which the user has registered with VPS 120. For example, information associated with the profile may further include information associated with the user (e.g., a username, password, PIN, etc.), information associated with each user device 110, such as a respective identifier (e.g., a mobile directory number (MDN), an Internet protocol (IP) address, a media access control (MAC) address, a CODEC identifier, etc.), and/or information associated with a type of user device 110, such as a computer device (e.g., a lap top computer, a tablet computer, etc.), a wireless mobile device (e.g., a Droid®, a Blackberry®, an iPhone®, etc.), a set top box, a gaming device, etc.

The information associated with the profile may also include a respective user history (e.g., prior purchases, prior URLs accessed, prior downloads, etc.) associated with each user device 110; information associated with services for which user device 110 has subscribed; information associated with a location (e.g., an address, a zip code, a city, etc.) of the user and/or user device 110; information associated user account limits, restrictions, etc.; information associated with a language spoken by the user; etc.

Billing server 250 may include one or more server devices, or other types of computation or communication devices, that gather, process, search, store, and/or provide information in a manner similar to that described herein. Billing server 250 may, for example, perform billing operations associated with accounts that correspond to each user device 110 associated with a user. For example, billing server 250 may receive an indication that user device 110 (e.g., a computer device), associated with the user, downloaded a video asset (e.g., via a broadband service associated with service provider network 140) as a result of a transaction via the store front portal. Billing server 250 may generate billing information that identifies the video asset, the type of transaction (e.g., a purchase, rental, subscription, etc.), a price associated with the transaction, a time at which the transaction occurred, etc. Billing server 250 may associate the billing information with an account that corresponds to the user and/or user device 110. Billing server 250 may generate other billing information regarding another transaction with another user device 110 (e.g., a set top box) with which the user is associated. Billing server 250 may associate the other billing information with another account that corresponds to the user and/or the other user device 110. In yet another example, billing server 250 may process payment information (e.g., based on credit card information, debit card information, etc.) associated with a transaction with a further user device 110 to purchase, rent, subscribe to, etc. another video asset.

Although FIG. 2 shows example components of VPS 120, in other implementations, VPS 120 may include fewer components, different components, differently arranged components, or additional components than depicted in FIG. 2. Additionally or alternatively, one or more components of VPS 120 may perform functions described as being performed by one or more other components of VPS 120.

Figure 3:
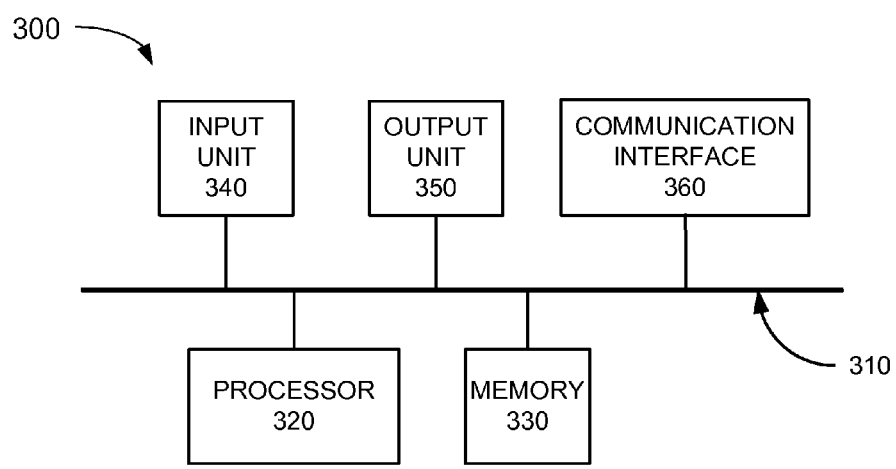
FIG. 3 is a diagram illustrating example components of a device that corresponds to one or more of the components of FIG. 2.

FIG. 3 is a diagram of example components of a device 300 that may correspond to user device 110, content provider 130, application server 210, IMG server 220, VOD server 225, CDN server 230, catalog server 235, VCM server 240, profile server 245, and/or billing server 250. Alternatively, each of user device 110, content provider 130, application server 210, IMG server 220, VOD server 225, CDN server 230, catalog server 235, VCM server 240, profile server 245, and/or billing server 250 may include one or more devices 300.

As shown in FIG. 3, device 300 may include a bus 310, a processor 320, a memory 330, an input unit 340, an output unit 350, and a communication interface 360. Bus 310 may include a path that permits communication among the components of device 300. Processor 320 may include a single-core processor, multi-core processor, microprocessor, and/or processing logic that may interpret and execute instructions. Memory 330 may include any type of dynamic storage device that may store information and instructions, for execution by processor 320, and/or any type of non-volatile storage device that may store information for use by processor 320.

Input unit 340 may include a mechanism that permits a user to input information to device 300, such as a keyboard, a keypad, a button, a switch, etc. Output unit 350 may include a mechanism that outputs information to the user, such as a display, a speaker, one or more light emitting diodes (LEDs), etc. Communication interface 360 may include any transceiver-like mechanism that enables device 300 to communicate with other devices and/or systems via wireless communications (e.g., radio frequency, infrared, and/or visual optics, etc.), wired communications (e.g., conductive wire, twisted pair cable, coaxial cable, transmission line, fiber optic cable, and/or waveguide, etc.), or a combination of wireless and wired communications. For example, communication interface 360 may include mechanisms for communicating with another device or system via a network, such as service provider network 140 and/or network 150. In one alternative implementation, communication interface 360 may be a logical component that includes input and output ports, input and output systems, and/or other input and output components that facilitate the transmission of data to other devices.

As will be described in detail below, device 300 may perform certain operations relating to video content. Device 300 may perform these operations in response to processor 320 executing software instructions contained in a computer-readable medium, such as memory 330. A computer-readable medium may be defined as a non-transitory memory device. A memory device may include space within a single physical memory device or spread across multiple physical memory devices. The software instructions may be read into memory 330 from another computer-readable medium or from another device. The software instructions contained in memory 330 may cause processor 320 to perform processes described herein. Alternatively, hardwired circuitry may be used in place of or in combination with software instructions to implement processes described herein. Thus, implementations described herein are not limited to any specific combination of hardware circuitry and software.

Although FIG. 3 shows example components of device 300, in other implementations, VPS 120 may include fewer components, different components, differently arranged components, or additional components than depicted in FIG. 3. Additionally or alternatively, one or more components of device 300 may perform functions described as being performed by one or more other components of device 300.

Figure 4:
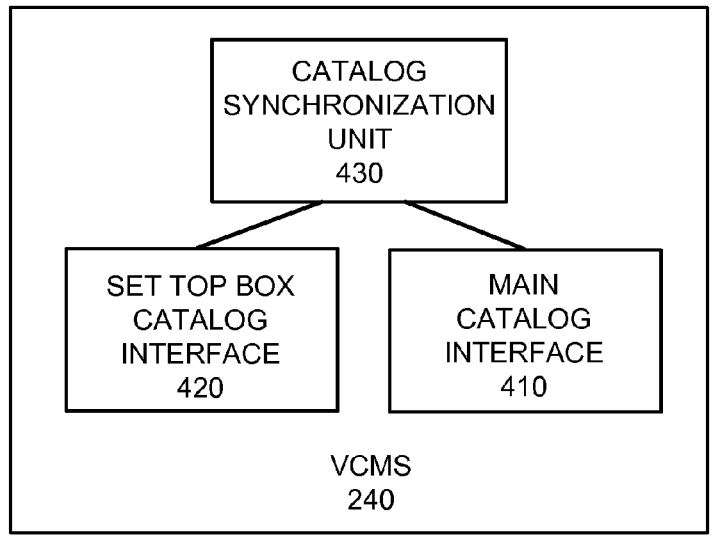
FIG. 4 is a diagram of example functional components of the video content management server of FIG. 2.

FIG. 4 is a diagram of example functional components of VCM server 240. The functional components of VCM server 240 may be implemented as a result of processor 320 executing instructions from memory 330. As shown in FIG. 4, VCM server 240 may include a main catalog interface 410, a set top box catalog interface 420, and a catalog synchronization unit 430.

Main catalog interface 410 may interface with catalog server 235. For example, main catalog interface 410 may process metadata associated with video assets into a format compatible with catalog server 235 and may provide the metadata to catalog server 235. Catalog interface 410 may also obtain metadata from catalog server 235 during an operation to synchronize catalog server 235 with STB catalog 226.

Set top box catalog interface 420 may interface with STB catalog 226. For example, set top box catalog interface 420 may process metadata associated with video assets into a format compatible with VOD server 225 and may provide the metadata to VOD server 225. Set top box catalog interface 420 may also obtain metadata from STB catalog 226 of VOD server 225 during an operation to synchronize catalog server 235 with STB catalog 226.

Catalog synchronization unit 430 may synchronize catalog server 235 and STB catalog 226. For example, catalog synchronization unit 430 may receive instructions to synchronize catalog server 235 and STB catalog 226. In one example, the instructions to synchronize catalog server 235 and STB catalog 226 may be executed at particular intervals (e.g., once a day, once a billing cycle, etc.). In another example, the instructions to synchronize catalog server 235 and STB catalog 226 may be executed in response to another trigger, such as an indication that either catalog server 235 or STB catalog 226 is out-of-date. For example, a user may report that a particular video asset is available in a catalog of video assets viewable through a set top box and is not available in a catalog of video assets viewable through a mobile communication device.

Catalog synchronization unit 430 may obtain a first set of metadata stored in catalog server 235, may obtain a second set of metadata stored in STB catalog 226, and may determine whether the first set of metadata matches a second set of metadata. When comparing metadata from catalog server 235 with metadata from STB catalog 226, catalog synchronization unit 430 need not compare all metadata fields. Rather, catalog synchronization unit 430 may select particular fields of metadata and may determine whether metadata from catalog server 235 matches metadata from STB catalog 226 by comparing the particular fields. Catalog synchronization unit 430 may identify particular metadata that is missing from either catalog server 235 or STB catalog 226 and may provide the missing metadata to the catalog from which the metadata is missing.

Although FIG. 4 shows example functional components of VCM server 240, in other implementations, VCM server 240 may include fewer functional components, different functional components, differently arranged functional components, or additional functional components than depicted in FIG. 4. Additionally or alternatively, one or more functional components of VCM server 240 may perform functions described as being performed by one or more other functional components of VCM server 240.

Figure 5:
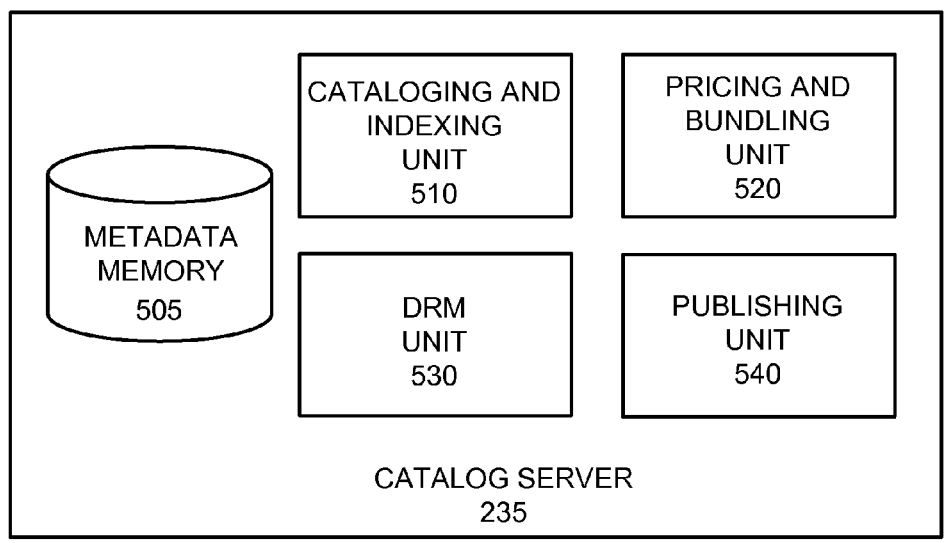
FIG. 5 is a diagram of example functional components of the catalog server of FIG. 2.

FIG. 5 is a diagram of example functional components of catalog server 235. The functional components of catalog server 235 may be implemented as a result of processor 320 executing instructions from memory 330. As shown in FIG. 5, catalog server 235 may include a metadata memory 505, a cataloging and indexing unit 510, a pricing and bundling unit 520, a DRM unit 530, and a publishing unit 540.

Metadata memory 505 may store metadata associated with video assets. Example information that may be stored in metadata memory 505 is described below with reference to FIG. 6.

Cataloging and indexing unit 510 may receive metadata from VCM server 240 and store the received metadata in metadata memory 505. Cataloging and indexing unit 510 may generate index information for the video asset. For example, cataloging and indexing unit 510 may generate one or more terms based on the metadata of the video asset, such as a description of the video asset, and may store the one or more terms in a searchable index of video assets, and/or may associate the video asset with one or more existing terms in the searchable index of video assets.

Pricing and bundling unit 520 may determine one or more prices for a video asset and may determine bundle information for the video asset. The prices may include a rental price (e.g., a price per single viewing, a price per day, per week, etc.), a sale price, a subscription price, etc. The prices may take into account, for example, operating expenses, settlement payments based on agreements with content providers 130, and/or a target profit margin. The bundle information may identify, for a video asset, another video asset that may be associated with the video asset. For example, the video asset and the other video asset may be purchased together as a bundle for a particular price.

DRM unit 530 may associate DRM-related information with the metadata associated with the merchandized assets. For example, DRM unit 530 may associate information associated with a license and/or a key (e.g., a private key, a public key, a CODEC, etc.) with the metadata for the merchandized video asset and may store the information associated with the license and/or the key in a memory associated with catalog server 235. The key may enable the video asset to be decrypted (e.g., by user device 110) when the information associated with the license indicates that the video asset can be decrypted and/or is otherwise available.

Publishing unit 540 may publish selected information from metadata memory 505 to application server 210. In one example, the selected information may include metadata associated with video assets being promoted by VPS 120, such as newly released video assets, popular video assets, video assets selected based on a user's interests and/or transaction history, and/or any other selected information. In another example, the selected information may include substantially all the information from metadata memory 505. In one example, publishing unit 540 may also publish information from metadata memory 505 to STB catalog 226. In another example, STB catalog 226 may obtain metadata associated with video assets directly from VCM server 240.

Although FIG. 5 shows example functional components of catalog server 235, in other implementations, catalog server 235 may include fewer functional components, different functional components, differently arranged functional components, or additional functional components than depicted in FIG. 5. Additionally or alternatively, one or more functional components of catalog server 235 may perform functions described as being performed by one or more other functional components of catalog server 235.

Figure 6:
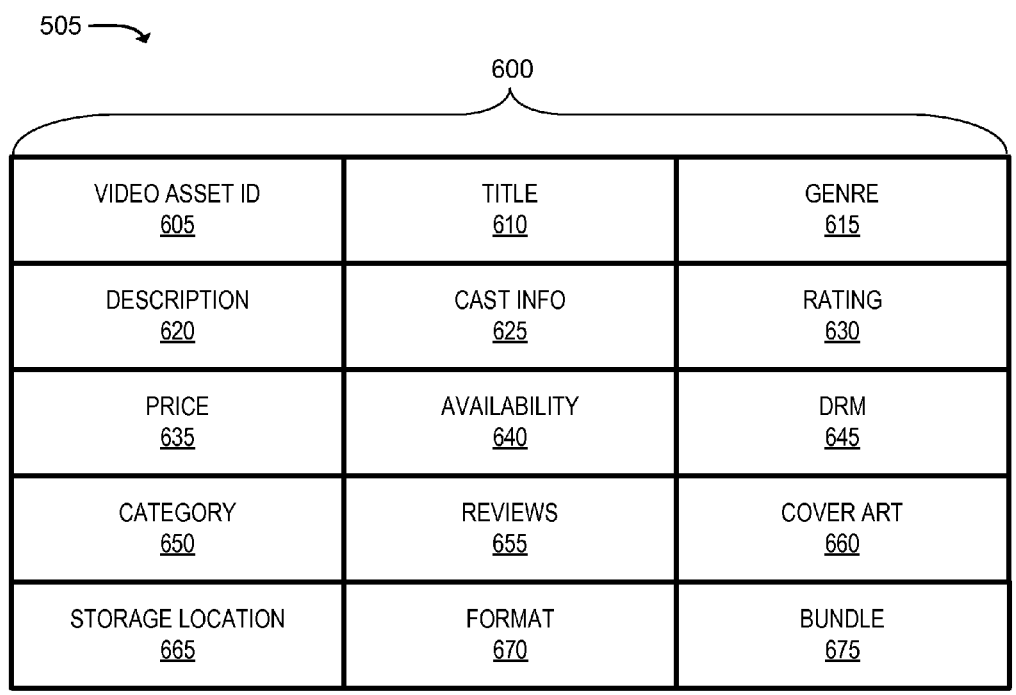
FIG. 6 is a diagram of example components of the metadata memory of FIG. 5.

FIG. 6 is a diagram of example fields that may be stored in metadata memory 505 of FIG. 5. In one example, metadata memory 505 may be implemented in a storage device included as part of memory 330 of catalog server 235. In another example, metadata memory 505 may be implemented in another storage device associated with another device or group of devices separate from, and possibly remote from, catalog server 235, such as memory 330 of STB catalog 226.

As shown in FIG. 6, metadata memory 505 may include video asset records 600 (referred to herein collectively as "video asset records 600" and individually as "video asset record 600"). Video asset record 600 may include a collection of fields, such as a video asset identifier (ID) field 605, a title field 610, a genre field 615, a description field 620, a cast information (info) field 625, a rating field 630, a price field 635, an availability field 640, a data rights management (DRM) field 645, a category field 650, a reviews field 655, a cover art field 660, a storage location field 665, a format field 670, and a bundle field 675.

Video asset ID field 605 may store a unique identifier (e.g., one or more sequences of characters, etc.) associated with a particular video asset and/or information associated with a particular content provider 130 from which the particular asset was received. Title field 610 may store a title associated with the particular video asset. Genre field 615 may store information associated with a genre that corresponds to the particular video asset. Description field 620 may store a description associated with the particular video asset, such as a summary of a movie when the particular video asset corresponds to the movie). Cast info field 625 may store information associated with an actor, a director, a producer, and/or other individuals associated with the particular video asset.a Rating field 630 may store information associated with a rating (e.g., general audience (G), parental guidance (PG), PG-13, restricted (R), mature audience (MA), etc.) that corresponds to the particular video asset. Price field 635 may store information, associated with one or more prices, that corresponds to the particular video asset. For example, one price may correspond to a sale price for the particular video asset. Another price may correspond to a rental price (e.g., a cost per viewing, per day, per week, etc.). One or more further prices may correspond to a price associated with a bundle of video assets and/or services that include the particular video asset, etc. Availability field 640 may store information associated with an availability of the particular asset. For example, availability field 640 store information that identifies when the particular video asset may be released to users of user devices 110 and when the particular asset is no longer available to users of user devices 110. In another example, availability field 640 may store information associated with a blackout period from a time when the particular asset is not to be released to another time when the particular asset may be released.

DRM field 645 may store license information associated with the particular asset and/or one or more keys that are used to encrypt the particular video asset. Category field 650 may store information associated with a category that corresponds to the particular video asset. The information, associated with the category, may include, for example, an indication that the particular video asset is a movie, a television program, a video game, etc. Reviews field 655 may include information associated with reviews, by users associated with VPS 120 and possibly users not associated with VPS 120, of the particular video asset. Cover art field 660 may include one or more images associated with the particular asset.

Storage location field 665 may store information associated with a location, within a memory associated with VOD server 225 and/or CDN server 230, that the particular video asset is stored. Format field 670 may store information associated with a video format that corresponds to the particular video asset. For example, format field 670 may store information associated with a bit rate, a screen size, a resolution level, a frame rate, a frame refresh rate, etc. that corresponds to the particular video asset. Bundle field 675 may store information, associated with a bundle, that identifies other services and/or other video assets, obtained from the ingested video content, that are associated with the particular video content. The bundle may be associated with a price identified in price field 635.

Although FIG. 6 shows example fields that may be stored in metadata memory 505, in other implementations, metadata memory 505 may include fewer fields, different fields, differently arranged fields, and/or additional fields than depicted in FIG. 6.

Figure 7:
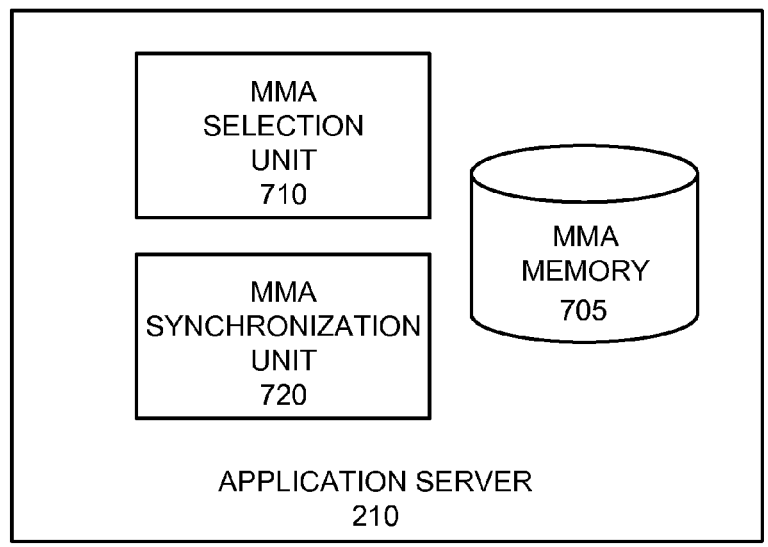
FIG. 7 is a diagram of example functional components of the application server of FIG. 2.

FIG. 7 is a diagram of example functional components of application server 210. The functional components of application server 210 may be implemented as a result of processor 320 executing instructions from memory 330. As shown in FIG. 7, application server 210 may include a media manager application (MMA) memory 705, an MMA selection unit 710, and an MMA synchronization unit 720.

MMA memory 705 may store media manager applications for particular user devices 110. Each type of user device 110, other than a set top box, may be associated with a particular media manager application. For example, with respect to mobile communication devices, a Droid® mobile communication device may be associated with a first media manager application, a Blackberry® mobile communication device may be associated with a second media manager application, an iPhone® mobile communication device, may be associated with a third media manager application, etc. As another example, with respect to personal computer devices, a computer running a Microsoft Windows® operating system may be associated with a first media manager application, a computer running a Mac OS® operating system may be associated with a second media manager application, a computer running a LINUX operating system may be associated with a third media manager application, etc.

MMA selection unit 710 may select a particular media manager application for a particular user device 110. For example, MMA selection unit 710 may determine a type of user device for a particular user device 110 and may select the particular media manager application based on the determined type of user device. In one example, MMA selection unit 710 may determine the type of user device by querying the user to select a type of user device from a list provided to the user. In another example, MMA selection unit 710 may select the type of user device automatically by, for example, analyzing information obtained from user device 110. For example, if user device 110 accesses a public store front associated with application server 110 using a browser application, MMA selection unit 710 may analyze a user agent string received from the browser application to determine a type of user device associated with user device 110.

MMA synchronization unit 720 may synchronize a registered user device 110 with other registered user devices 110 associated with a user profile. In one example, MMA synchronization unit 720 may synchronize a media manager application associated with a user device 110 with settings associated with a set top box. In another example, MMA synchronization unit 720 may synchronize a media manager application associated with a user device 110 with a media manager application of another user device 110 that does not correspond to a set top box.

For example, assume a user registers a first computer device with VPS 120 and uses the first computer device to purchase and consume video assets from VPS 120. At a later time, the user registers a second computer device and downloads a media manager application for the second computer device. MMA synchronization unit 720 may synchronize settings associated with the downloaded media manager application for the second computer device with settings associated with the media manager application of the first computer device. Furthermore, MMA synchronization unit 720 may cause one or more video assets, which have been downloaded to the first computer device, to be downloaded to the second computer device 110.

Although FIG. 7 shows example functional components of application server 210, in other implementations, application server 210 may include fewer functional components, different functional components, differently arranged functional components, or additional functional components than depicted in FIG. 7. Additionally or alternatively, one or more functional components of application server 210 may perform functions described as being performed by one or more other functional components of application server 210.

Figure 8:
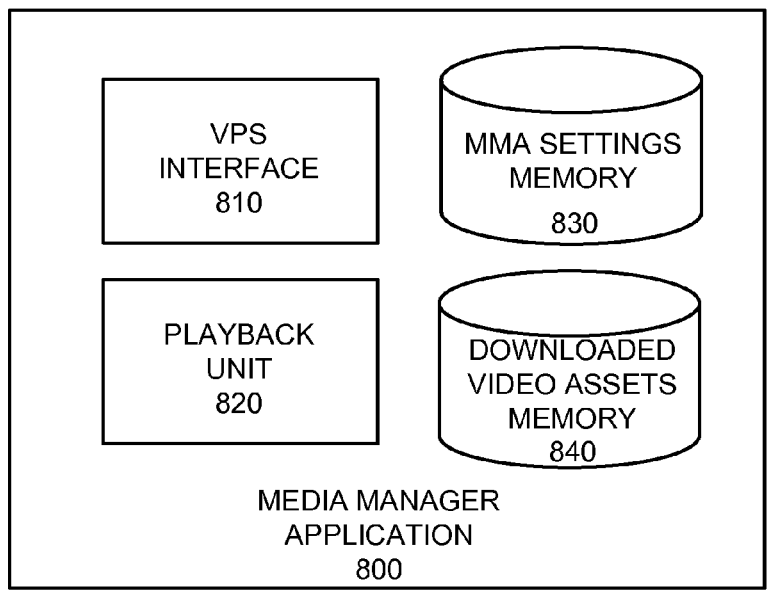
FIG. 8 is a diagram of example functional components of a media manager application associated with a user device of FIG. 1.

FIG. 8 is a diagram of example functional components of an MMA 800. MMA 800 may be selected for a particular user device 110 from MMA memory 705 by MMA selection unit 710 and may be downloaded and installed on the particular user device 110. The functional components of MMA 800 may be implemented as a result of processor 320 executing instructions from memory 330. As shown in FIG. 8, MMA 800 may include a VPS interface 810, a playback unit 820, an MMA settings memory 830, and a downloaded video assets memory 840.

VPS interface 810 may interact with VPS system 120. For example, VPS interface 810 may authenticate a user with VPS 120 by sending a username and password to application server 210 when the user activates MMA 800. VPS interface 810 may interact with a store front associated with application server 210 to present a catalog of available video assets on a display device of user device 110 running MMA 800. VPS interface 810 may send a request to application server 210 to purchase a video asset and may provide payment information to application server 210 (e.g., a credit card number). VPS interface 810 may also download and/or stream a purchased video asset to user device 110.

Playback unit 820 may consume a purchased video asset that has been downloaded to, or is being streamed to, user device 110. MMA settings memory 830 may store one or more settings associated with MMA 800. Example information that may be stored in MMA settings memory 830 is described below with reference to FIG. 9. Downloaded video assets memory 840 may store purchased video assets that have been downloaded to user device 110.

Although FIG. 8 shows example functional components of MMA 800, in other implementations, MMA 800 may include fewer functional components, different functional components, differently arranged functional components, or additional functional components than depicted in FIG. 8. Additionally or alternatively, one or more functional components of MMA 800 may perform functions described as being performed by one or more other functional components of MMA 800.

Figure 9:
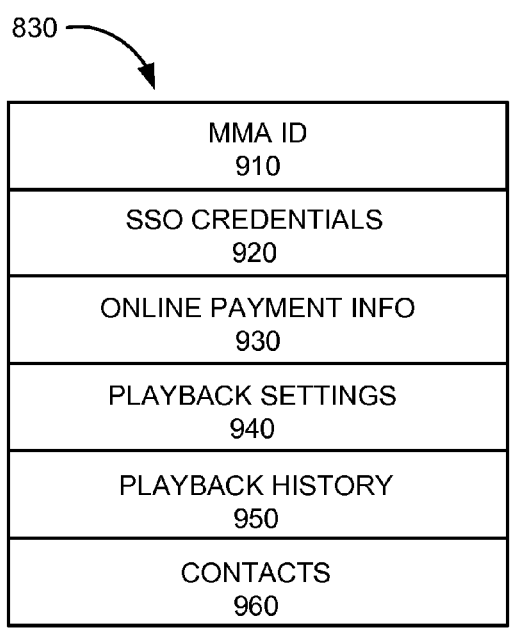
FIG. 9 is a diagram of example components of the media manager application settings memory of FIG. 8.

FIG. 9 is a diagram of example fields that may be stored in MMA settings memory 830 of FIG. 8. In one example, MMA settings memory 830 may be implemented in a storage device included as part of memory 330 of user device 110. In another example, MMA settings memory 830 may be implemented in another storage device associated with another device or group of devices separate from, and possibly remote from, user device 110.

As shown in FIG. 9, MMA settings memory 830 may include an MMA ID field 910, a single sign-on (SSO) credentials field 920, an online payment information field 930, a playback settings field 940, a playback history field 950, and a contacts field 960.

MMA ID field 910 may store an identifier that uniquely identifies a particular media manager application. The identifier may be used by application server 210 to associate the particular media manager application with a particular type of user device. Furthermore, MMA ID field 910 may include an identifier that uniquely identifies a particular user device. For example, MMA ID field 910 may include a MAC address associated with the user device, an IP address associated with the user device, and/or a mobile communication device identifier, such as a Mobile Subscriber Integrated Services Digital Network number (MSISDN), an International Mobile Subscriber Identity (IMSI) number, a mobile identification number (MIN), or an International Mobile Equipment Identifier (IMEI), an Integrated Circuit Card Identifier (ICCI), and/or any other mobile communication device identifier.

SSO credentials field 920 may include SSO credentials, such as a username and password, which may be used by MMA 800 to authenticate the user device with application server 210. Online payment information field 930 may include information that may be used by the user of user device to purchase video assets from VPS 120 using an online payment system. For example, online payment information field 930 may store credit card information.

Playback settings field 940 may store one or more playback settings associated with playback of video assets. For example, playback settings field 940 may store a volume setting, a subtitles setting, a video quality setting, a download speed setting, and/or any other setting associated with MMA 800.

Playback history field 950 may store information about the playback history of one or more video assets. For example, playback history field 950 may store information about whether or not a particular video asset has been played, a date and time when the particular video asset has been played, a bookmark associated with a particular video asset (where the bookmark indicates a place at which the user stopped playing the video asset), and/or any other playback history information associated with the particular video asset.

Contacts field 960 may store one or more contacts (e.g., other users) associated with MMA 800. For example, MMA 800 may enable the user to exchange text messages with another user while watching a same video asset. As another example, MMA 800 may allow the user to play online games with other users.

Although FIG. 9 shows example fields that may be stored in MMA settings memory 830, in other implementations, MMA settings memory 830 may include fewer fields, different fields, differently arranged fields, and/or additional fields than depicted in FIG. 9.

Figure 10:
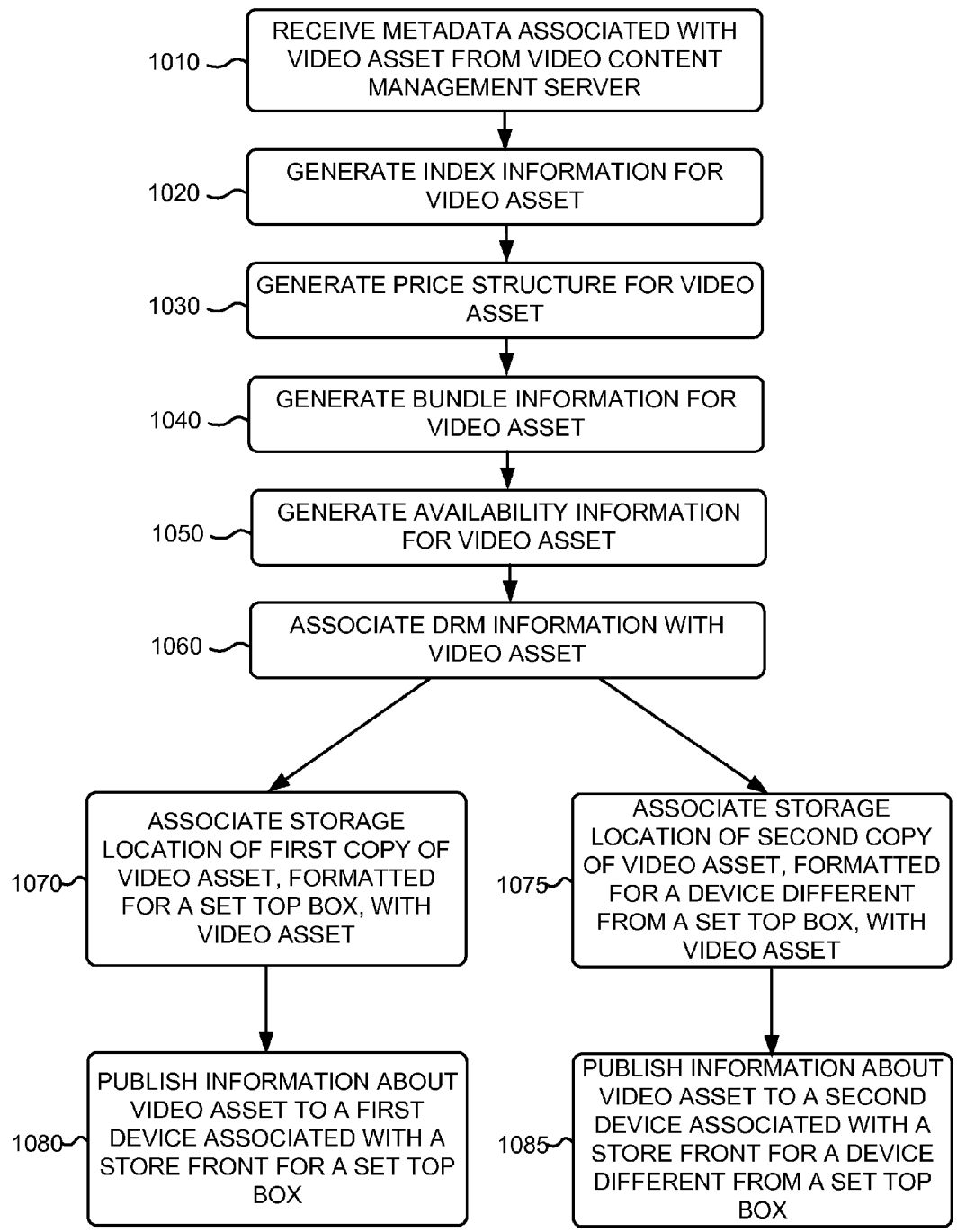
FIG. 10 is a flow chart of an example process for processing metadata associated with a video asset according to an implementation described herein.

FIG. 10 is a flow chart of an example process for processing metadata associated with a video asset according to an implementation described herein. In one implementation, the process of FIG. 10 may be performed by VPS 120. In other implementations, some or all of the process of FIG. 10 may be performed by another device or a group of devices separate from and/or possibly remote from VPS 120 and/or including VPS 120.

The process of FIG. 10 may include receiving metadata associated with a video asset from a video content management server (block 1010). For example, catalog server 235 may receive metadata associated with a video asset from VCM server 240. The received metadata may include, for example, one or more of a video asset identifier, a title associated with the video asset, a genre associated with the video asset, a category associated with the video asset, a description associated with the video asset, cast information associated with the video asset, rating information associated with the video asset, review information associated with the video asset, cover art associated with the video asset, an availability associated with the video asset, DRM information associated with the video asset, storage locations of one or more copies of the video asset, a format associated with the video asset, bundle information associated with the video asset, and/or any other metadata associated with the video asset.

The metadata may further include settlement information associated with the video asset. The settlement information may include information about any agreements and/or contracts with a content provider associated with the video asset. The settlement information may include, for example, a specification of what percentage of each purchase associated with the video asset should be paid to the content provider.

Index information for the video asset may be generated (block 1020). For example, cataloging and indexing unit 510 of catalog server 235 may determine one or more index terms for the video asset based on the metadata (e.g., based on the description, casting information, category, genre, etc.), may add the index terms to a searchable index, and may associate the video asset with the index terms. If one or more of the index terms already exist in the searchable index, cataloging and indexing unit 510 may associate the video asset with the index terms. The indexing information may be stored, for example, in description field 620 of video asset record 600.

A price structure for the video asset may be generated (block 1030). For example, pricing and bundling unit 520 may determine one or more prices for the video asset. For example, pricing and bundling unit 520 may determine a purchase price and/or one or more rental prices for one or more rental periods. If the video asset corresponds to an a video asset with renewable content (e.g., a particular television channel, a particular television show, broadcasts associated with a particular sport or a particular sports team, an online game, etc.), pricing and bundling unit 520 may determine one or more subscription prices for the video asset. The determined prices may take into account one or more factors, including, for example, operating expenses associated with VPS 120, settlement information associated with a content provider of the video asset, a target profit margin associated with VPS 120, one or more promotions being offered by VPS 120, and/or any other factor that may affect the price of a video asset. The price information may be stored in price field 635 of video asset record 600.

Bundle information for the video asset may be generated (block 1040). For example, pricing and bundling unit 520 may determine one or more bundles associated with the video asset and one or more bundle prices associated with the determined one or more bundles. As an example, a television show episode may be bundled with other episodes from the same season into a bundle package offered at one price. As another example, two movies may have been purchased together or within a particular period of time by a particular number of users. As a result, the two movies may be bundled together and offered for a single price. As yet another example, two or more television channels may be bundled together and offered for a single subscription price. The bundle information may be stored, for example, in bundle field 675 of video asset record 600.

Availability information for the video asset may be generated (block 1050). For example, pricing and bundling unit 520 may determine a date at which a video asset becomes available based on an agreement with a content provider of the video asset. The availability information may be stored, for example, in availability field 640 of video asset record 600.

DRM information may be associated with the video asset (block 1060). For example, catalog server 235 may obtain, from VCM server 240, license information that identifies terms and/or conditions for handling, promoting, distributing, and/or using the video asset and/or enables the video asset to be encrypted and/or decrypted (e.g., based on keys associated with the license information). Catalog server 235 may store the license information in DRM field 645 of video asset record 600. Furthermore, catalog server 235 may generate a key (e.g., a private key, a public key, a CODEC, etc.) for the video asset and store the key in DRM field 645 of video asset record 600. The key may enable the video asset to be decrypted (e.g., by user device 110) when the information associated with the license indicates that the video asset can be decrypted and/or is otherwise available.

A storage location of a copy of the video asset formatted for a set top box may be associated with the video asset (block 1070). For example, VCM server 240 may generate a first copy of the video asset formatted for a set top box and may provide information about a storage location of the first copy of the video asset, such as a URL, to catalog server 235. Catalog server 235 may store information about the location of the first copy in storage location field 665 of video asset record 600.

A storage location of a copy of the video asset formatted for a device different from a set top box may be associated with the video asset (block 1075). For example, VCM server 240 may generate a second copy of the video asset formatted for a device other than a set top box (e.g., a personal computer, mobile communication device, gaming console, etc.) and may provide information about a storage location of the second copy of the video asset, such as a URL, to catalog server 235. Catalog server 235 may store information about the location of the second copy in storage location field 665 of video asset record 600. While not shown in FIG. 10, VCM server 240 may generate additional copies of the video asset in additional formats (e.g., for another type of user device) and catalog server 235 may store information about the additional copies in storage location field 665 of video asset record 600.

Information about the video asset may be published to a device associated with a store front for a set top box (block 1080). For example, VOD server 225 may maintain a store front of video assets for set top boxes and catalog server 235 may publish some or all of the information from video asset record 600 to VOD server 225.

Information about the video asset may be published to a device associated with a store front for a device different from a set top box (block 1085). For example, application server 210 may maintain a store front of video assets for devices different from a set top box (e.g., personal computer, mobile communication device, gaming console, etc.) and catalog server 235 may publish some or all of the information from video asset record 600 to application server 210. Furthermore, application server 210 may maintain multiple store fronts (e.g., different store fronts for different device types) and catalog server 235 may publish the information from video asset record 600 to each of the multiple store fronts.

In one example, the information that may be published to VOD server 225 and to application server 210 may include information associated with a subset of video assets. The subset of video assets may include, for example, video assets currently being promoted by VPS 120 or by a content provider 130, video assets that have recently been released, video assets that are popular (e.g., based on purchases made by users), video assets that are highly rated by users, etc. The subset of video assets may be presented by a store front on a home page of the store front when a user device 110 first accesses the store front. If a user proceeds to browse the store front or submits a search query to the store front, the store front may request additional information from the catalog. For example, VOD server 225 may request the additional information from STB catalog 226 and application server 210 may request the additional information from catalog server 235.

In one example, VOD server 225 may not include STB catalog 226 and the store front provided by VOD server 225 and accessible from set top boxes may interact directly with catalog server 235. In another example, catalog server 235 may publish some or all of the information to STB catalog 226 the store front provided by VOD server 225 may interact with STB catalog 226. In yet another example, STB catalog 226 may receive metadata from VCM server 240 and may process the metadata independently from catalog server 235. In other words, blocks 1010-1060, 1070, and 1080 of FIG. 10 may be performed by STB catalog 226 of VOD server 225 independently of catalog server 235.

Figure 11:
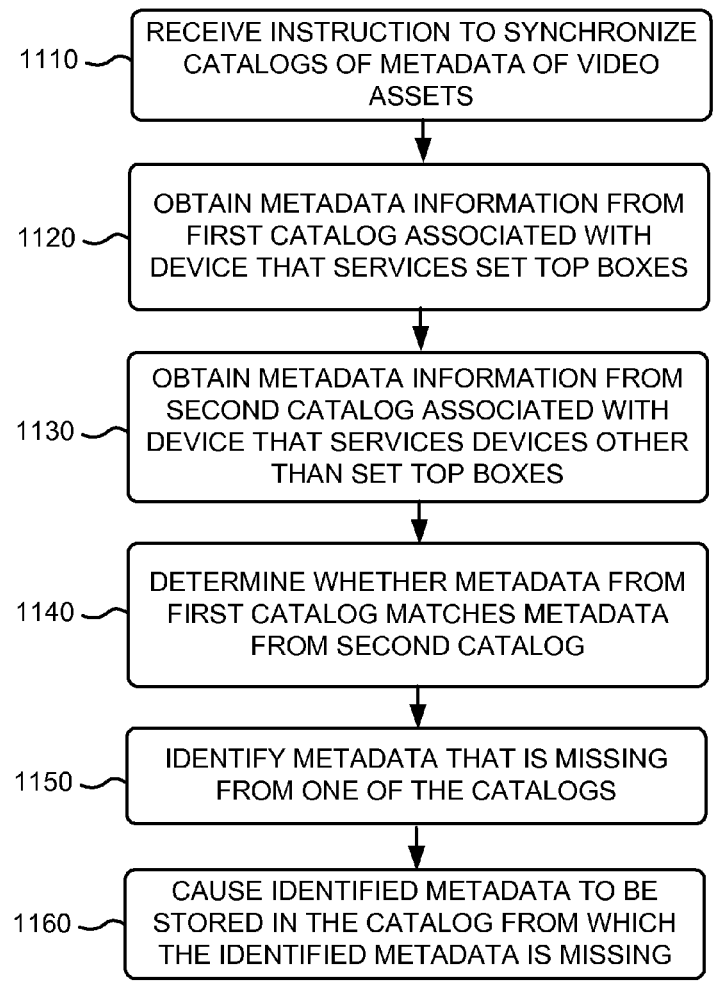
FIG. 11 is a flow chart of an example process for synchronizing catalogs of metadata of video assets according to an implementation described herein.

FIG. 11 is a flow chart of an example process for synchronizing catalogs of metadata of video assets according to an implementation described herein. In one implementation, the process of FIG. 11 may be performed by VPS 120. In other implementations, some or all of the process of FIG. 11 may be performed by another device or a group of devices separate from and/or possibly remote from VPS 120 and/or including VPS 120.

The process of FIG. 11 may include receiving an instruction to synchronize catalogs of metadata of video assets (block 1110). For example, VCM server 240 may receive an instruction to synchronize catalog server 235 and STB catalog 226 at particular intervals (e.g., once a day, once a billing cycle, etc.). In another example, the instructions to synchronize catalog server 235 and STB catalog 226 may be executed in response to another trigger, such as an indication that either catalog server 235 or STB catalog 226 is out-of-date. For example, a user may report that a particular video asset is available in a catalog of video assets viewable through a set top box and is not available in a catalog of video assets viewable through a mobile communication device.

Metadata information may be obtained from a first catalog associated with a device that services set top boxes (block 1120). For example, catalog synchronization unit 430 of VCM server 240 may obtain a first set of metadata from video asset records 600 stored by STB catalog 226. Metadata information may be obtained from a second catalog associated with a device that services devices other than set top boxes (block 1130). For example, catalog synchronization unit 430 of VCM server 240 may obtain a second set of metadata from video asset records 600 stored by catalog server 235.

A determination may be made as to whether the metadata from the first catalog matches the metadata from the second catalog (block 1140). For example, catalog synchronization unit 430 may compare the metadata from STB catalog 226 with the metadata from catalog server 235. Catalog synchronization unit 430 need not compare all metadata fields of video asset records 600. Rather, catalog synchronization unit 430 may select particular fields of metadata and may determine whether metadata from catalog server 235 matches metadata from STB catalog 226 by comparing the particular fields. Furthermore, catalog synchronization unit 430 may optimize the comparison by comparing hashes or fingerprints of the metadata rather than the metadata itself.

Metadata that is missing from one of the catalogs may be identified (block 1150). If the metadata from STB catalog 226 and the metadata from catalog server 235 do not match, catalog synchronization unit 430 may identify missing metadata. For example, catalog synchronization unit 430 may determine that a video asset record 600, or information in a particular field of video asset record 600, exists in one of the catalog and does not exist in the other catalog. The identified metadata may be stored in the catalog from which the identified metadata is missing (block 1160). For example, VCM server 240 may instruct the catalog that includes the metadata to provide the metadata to the other catalog that does not include the metadata.

Figure 12A:
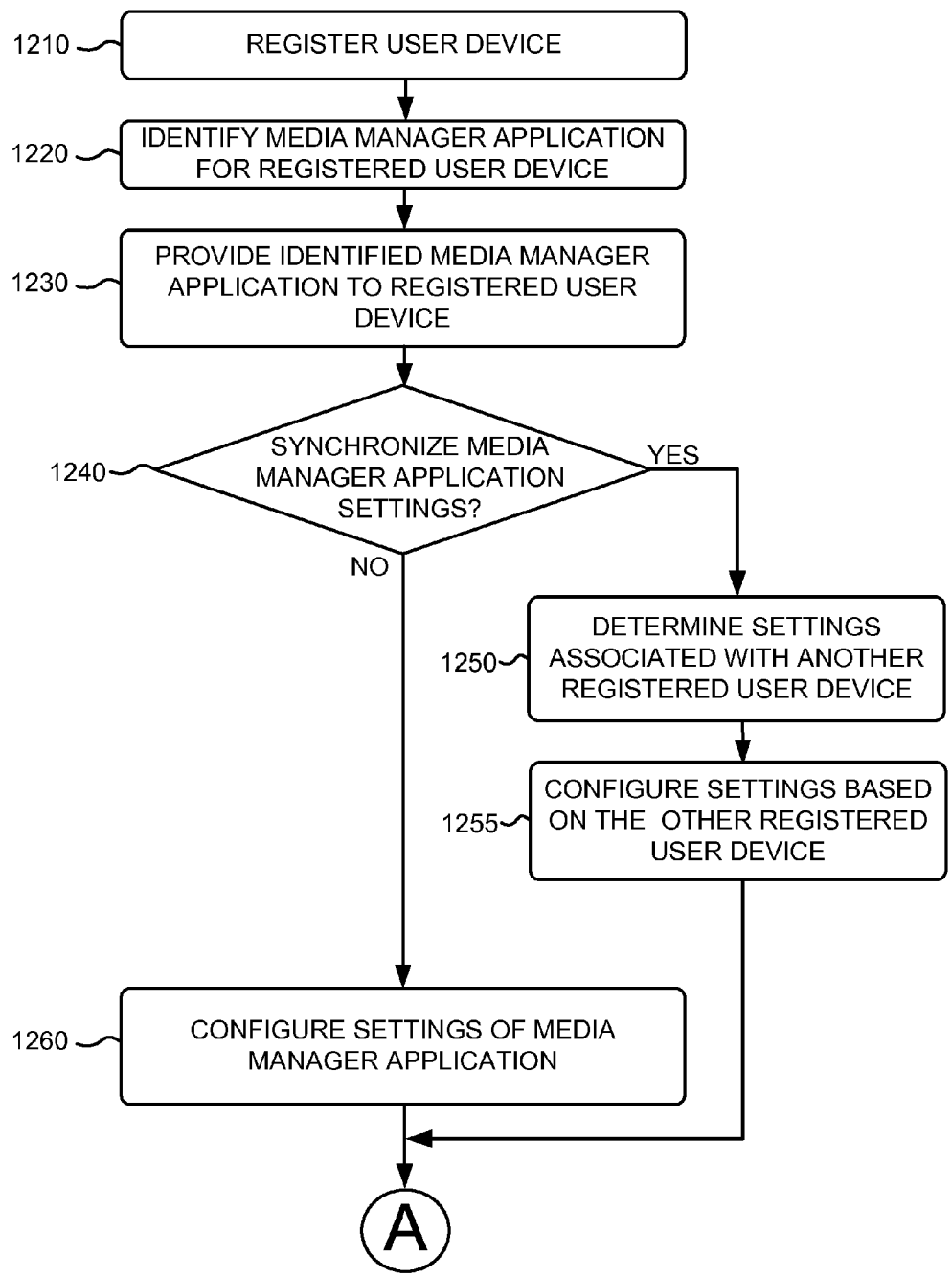
FIGS. 12A and 12B are flow charts of an example process for synchronizing media manager applications for a user according to an implementation described herein.
Figure 12B:
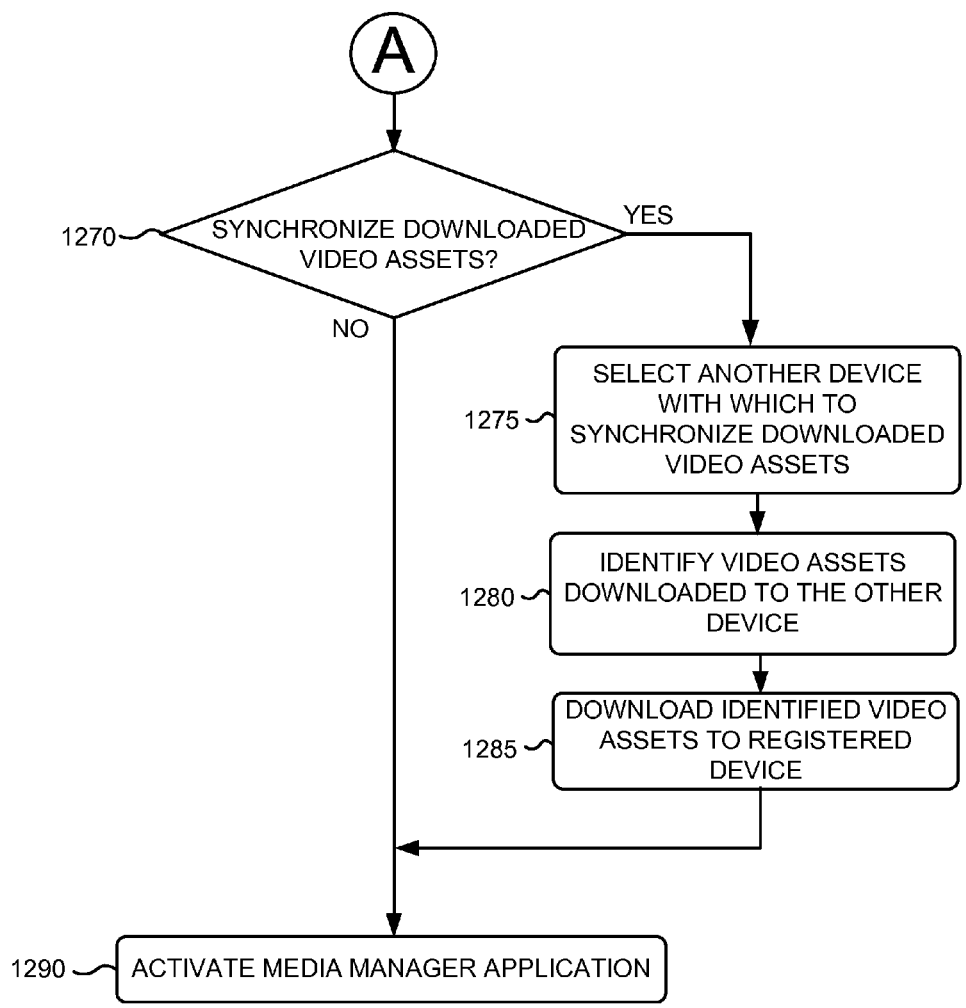

FIGS. 12A and 12B are flow charts of an example process for synchronizing media manager applications for a user according to an implementation described herein. In one implementation, the process of 12A and 12B may be performed by VPS 120. In other implementations, some or all of the process of 12A and 12B may be performed by another device or a group of devices separate from and/or possibly remote from VPS 120 and/or including VPS 120.

The process of FIG. 12A may include registering a user device (block 1210). For example, a user may access a public store front associated with application server 210 by typing a URL of the public store front into an address bar of a browser application running on user device 110. Application server 210 may provide a home page of the store front, which may allow the user to log in. The user may enter a username and password and application server 210 may authenticate the user. The user may be provided with an option to register user device 110 with the user's profile. If the user selects to register user device 110, application server 210 may instruct profile server 245 to add user device 110 to the user's profile.

A media manager application may be identified for the registered user device (block 1220). For example, MMA selection unit 710 may identify a user device type associated with user device 110. In one example, MMA selection unit 710 may determine the user device type by prompting the user to specify a user device type. In another example, MMA selection unit 710 may automatically determine the user device type. As an example, MMA selection unit 710 may analyze a message received from user device 110, such as a user agent string received from the browser application of user device 110. As another example, MMA selection unit 710 may send a query to user device 110 to determine the user device type. MMA selection unit 710 may access MMA memory 705 to identify a particular media manager application associated with the determined user device type.

The identified media manager application may be provided to the registered user device (block 1230). For example, MMA selection unit 710 may provide the selected media manager application to user device 110. User device 110 may download the selected media manager application.

A determination may be made as to whether to synchronize media manager application settings (block 1240). For example, MMA synchronization unit 720 may determine whether there is another user device 110 associated with the user profile. If no other user device 110 is registered with the user profile, there may be no need to synchronize the downloaded media manager application. If there is another user device 110 registered with the user profile, MMA synchronization unit 720 may provide an option to the user to synchronize the settings of the downloaded media manager application with settings associated with the other registered user device 110.

If it is determined that media manager application settings are to be synchronized (block 1240—YES), settings associated with another registered user device may be determined (block 1250). For example, a user may select to synchronize the settings of the downloaded media manager applications. MMA synchronization unit 720 may access the other registered user device 100 to retrieve settings associated with the other user device 110. For example, if the other user device 110 corresponds to a set top box, MMA synchronization unit 720 may retrieve settings associated with the set top box. As another example, if the other user device 110 corresponds to a user device 110 with an installed media manager application, MMA synchronization unit 720 may access MMA settings memory 830 associated with MMA 800 installed on the other user device 110. For example, MMA synchronization unit 720 may retrieve SSO credentials, online payment information, playback settings, playback history, and/or contacts information from MMA settings memory 830 of the other user device 110.

Settings may be configured based on the other registered user device (block 1255). For example, MMA synchronization unit 720 may store the retrieved information from MMA settings memory 830 of the other user device 110 in MMA settings memory 830 of the newly registered user device 110. Processing may continue to FIG. 12B.

Returning to block 1240, if it is determined that media manager application settings are not to be synchronized (block 1240—NO), settings for the media manager application may be configured (block 1260). For example, the user may be prompted to manually enter one or more settings for the installed media manager application. As another example, default settings may be selected.

Continuing to FIG. 12B, a determination may be made as to whether to synchronize downloaded video assets (block 1270). A determination may be made as to whether the user has downloaded any video assets to another user device 110 registered with the user profile. For example, MMA synchronization unit 720 may access downloaded video assets memory 840 of other registered user devices 110 associated with the user profile. If the user has not downloaded any video assets, no synchronization of downloaded video assets may be required. If the user did download video assets, the user may be provided with the option to download the video assets to the newly registered user device 110.

If it is determined that downloaded video assets are to be synchronized (block 1270—YES), another device may be selected with which to synchronize downloaded video assets (block 1275). For example, the user may select another device with which to synchronize the downloaded video assets. MMA synchronization unit 720 may select another user device 110. Video assets downloaded to the other device may be identified (block 1280). For example, MMA synchronization unit 720 may access MMA settings memory 830 of the identified user device 110 and determine identifiers of video assets that have been downloaded to MMA settings memory 830.

The identified video assets may be downloaded to the registered device (block 1285). For example, MMA synchronization unit 720 may download the identifier video assets to the newly registered user device 110. The user may be prompted to select which of the identifier video assets are to be downloaded. Processing may continue to block 1290.

If it is determined that downloaded video assets are not to be synchronized (block 1270—NO), processing may continue to block 1290. The media manager application may be activated (block 1290). For example, application server 210 may designate the downloaded media manager application as being ready for use. The user may now use the media manager application to browse a catalog of video assets via a store front, purchase a video asset using the media manager application, and/or view a purchased asset using the media manager application.

The foregoing description provides illustration and description, but is not intended to be exhaustive or to limit the implementations to the precise form disclosed. Modifications and variations are possible in light of the above teachings or may be acquired from practice of the embodiments.

While series of blocks have been described with respect to FIGS. 10, 11, 12A and 12B, the order of the blocks may be modified in other implementations. Further, non-dependent blocks may be performed in parallel.

It will be apparent that systems and/or methods, as described above, may be implemented in many different forms of software, firmware, and hardware in the implementations illustrated in the figures. The actual software code or specialized control hardware used to implement these systems and methods is not limiting of the embodiments. Thus, the operation and behavior of the systems and methods were described without reference to the specific software code—it being understood that software and control hardware can be designed to implement the systems and methods based on the description herein.

Further, certain portions, described above, may be implemented as a component that performs one or more functions. A component, as used herein, may include hardware, such as a processor, an ASIC, or a FPGA, or a combination of hardware and software (e.g., a processor executing software).

It should be emphasized that the terms "comprises"/"comprising" when used in this specification are taken to specify the presence of stated features, integers, steps or components but does not preclude the presence or addition of one or more other features, integers, steps, components or groups thereof.

Even though particular combinations of features are recited in the claims and/or disclosed in the specification, these combinations are not intended to limit the disclosure of the embodiments. In fact, many of these features may be combined in ways not specifically recited in the claims and/or disclosed in the specification. Although each dependent claim listed below may directly depend on only one other claim, the disclosure of the embodiments includes each dependent claim in combination with every other claim in the claim set.

No element, act, or instruction used in the present application should be construed as critical or essential to the embodiments unless explicitly described as such. Also, as used herein, the article "a" is intended to include one or more items. Where only one item is intended, the term "one" or similar language is used. Further, the phrase "based on" is intended to mean "based, at least in part, on" unless explicitly stated otherwise.

What is claimed is:

1. A method comprising:
   receiving, by a video provisioning system, metadata associated with a plurality of video assets;
   generating a plurality of first copies of the video assets in a first format corresponding to set top boxes;
   generating a plurality of second copies of the video assets in a second format corresponding to devices other than the set top boxes;
   creating a plurality of first video asset records containing:
   fields including the metadata,
   a field including information indicating the first format, and
   a field including information identifying a first storage location of the first copies;
   creating a plurality of second video asset records containing:
   fields including the metadata,
   a field including information indicating the second format, and
   a field including information identifying a second storage location of the second copies;
   storing, by the video provisioning system, the plurality of first video asset records in a first catalog of video assets and the plurality of second video asset records in a second catalog of video assets, available through the video provisioning system;
   publishing, by the video provisioning system, information from the stored first video asset records to a first device that hosts a video assets store front for the set top boxes;
   publishing, by the video provisioning system, information from the stored second video asset records to a second device that hosts a video assets store front for the devices other than the set top boxes, wherein the second device is different from the first device;
   receiving, by the video provisioning system, user input indicating that information, regarding a video asset, is published in one of the first catalog or the second catalog and is not published in the other one of the first catalog or the second catalog; and
   synchronizing, by the video provisioning system and responsive to the user input, the first and second catalogs with respect to the video asset.

2. The method of claim 1, wherein the metadata is received from a video content management server that receives the plurality of video assets from content providers of the video assets.

3. The method of claim 1, further comprising:
   generating a price structure for the video asset; and
   including information about the price structure in the metadata associated with the video asset.

4. The method of claim 1, further comprising:
   generating index information for the video asset, where generating index information for the video asset includes indexing the video asset with respect to one or more terms associated with the video asset.

5. The method of claim 1, further comprising:
generating bundle information for the video asset, where the bundle information includes information about another video asset that can be purchased together with the video asset; and
including information about the bundle information in the metadata associated with the video asset.

6. The method of claim 1, further comprising:
including information about digital rights management, associated with the video asset, in the metadata associated with the video asset.

7. The method of claim 1, wherein creating a first video asset record containing fields including the metadata and creating a second video asset record containing fields including the metadata comprises:
storing, in one or more of the fields of the first video asset record corresponding to one or more of the fields of the second video asset record, information from the metadata which is common to the first copy of the video asset and the second copy of the video asset.

8. A video provisioning system comprising:
a server device to:
receive metadata associated with a plurality of video assets;
generate multiple copies of the video assets in multiple formats,
create, for each of the copies, a data structure containing:
fields including the metadata,
a field including information indicating the format of the copy, and
a field including information identifying a storage location of the copy,
store the data structures in respective catalogs corresponding to the multiple formats of the multiple copies of the video assets available through the video provisioning system;
publish information from a first data structure, corresponding to a first format of the multiple formats, to a first device that hosts a video assets store front for set top boxes;
publish information from a second data structure, corresponding to a second format of the multiple formats, to a second device that hosts a video assets store front for devices other than set top boxes, wherein the second device is different from the first device;
receive user input indicating that information, regarding a video asset, is published in a first catalog corresponding to the first format and is not published in a second catalog corresponding to a second format; and
synchronizing, responsive to the user input, the first and second catalogs with respect to the video asset.

9. The video provisioning system of claim 8, wherein the server device is further configured to:
generate a price structure for the video asset; and
include information about the price structure in the metadata associated with the video asset.

10. The video provisioning system of claim 8, wherein the server device is further configured to:
generate index information for the video asset,
wherein when generating the index information for the video asset, the server device is configured to index the video asset with respect to one or more terms associated with the video asset.

11. The video provisioning system of claim 8, wherein the server device is further configured to:
generate bundle information for the video asset, wherein the bundle information includes information about another video asset available for purchase together with the video asset; and
include information about the bundle information in the metadata associated with the video asset.

12. The video provisioning system of claim 8, wherein the server device is further configured to:
include information about digital rights management, associated with the video asset, in the metadata associated with the video asset.

13. The video provisioning system of claim 8, wherein the server device, when creating a data structure, is further configured to:
create a data structure containing fields including identical information for each of the copies for a corresponding field.

14. A method comprising:
receiving, by a server device associated with a video provisioning system, user input indicating that a video asset that is published in a first catalog of video assets corresponding to a first type of video format, is not published in a second catalog of video assets corresponding to a second type of video format,
executing, based on the user input, one or more instructions to synchronize the first and second catalogs associated with the video provisioning system;
obtaining, by the server device, a first plurality of metadata, associated with one or more video assets, from a first device that includes the first catalog of video assets, wherein the first catalog is accessible through a set top box;
obtaining, by the server device, a second plurality of metadata, associated with one or more video assets, from a second device that includes the second catalog of video assets, wherein the second catalog is accessible through a device other than a set top box;
determining, by the server device, whether the first plurality of metadata matches the second plurality of metadata;
identifying, by the server device, metadata that is not included in one of the first catalog or in the second catalog, when the first plurality of metadata does not match the second plurality of metadata; and
causing, by the server device, the identified metadata to be included in the one of the first catalog or the second catalog.

15. The method of claim 14, where the server device includes a video content management server that ingests video assets from content providers of video assets and provides metadata associated with the video assets to at least one of the first catalog or the second catalog.

16. The method of claim 14, wherein the identified metadata includes one or more of:
a description of a particular video asset;
a price structure associated with the particular video asset;
bundle information associated with the particular video asset;
information about a storage location of the particular video asset;
information regarding an availability of the particular video asset;
information about digital rights management associated with the particular video asset;

cover art associated with the particular video asset; a rating associated with the particular video asset; or a review associated with the particular video asset.

17. The method of claim 14, wherein the first and second plurality of metadata comprises information stored in multiple fields of a video asset record, and wherein determining whether the first plurality of metadata matches the second plurality of metadata comprises:

selecting fewer than all of the multiple fields; and performing a comparison of the first plurality of metadata to the second plurality of metadata using information stored in the selected fewer than all of the multiple fields.

18. A video provisioning system comprising:

a server device configured to:

receive user input indicating that a video asset that is published in a first catalog of video assets corresponding to a first type of video format, is not published in a second catalog of video assets corresponding to a second type of video format, execute, based on the user input, one or more instructions to synchronize the first and second catalogs of video assets;

obtain a first plurality of metadata, associated with the one or more video assets, from a first device that includes the first catalog of video assets, wherein the first catalog is accessible through a set top box;

obtain a second plurality of metadata, associated with one or more video assets, from a second device that includes the second catalog of video assets, wherein the second catalog is accessible through a device other than a set top box;

determine whether the first plurality of metadata matches the second plurality of metadata;

identify metadata that is not included in one of the first catalog or in the second catalog, when the first plurality of metadata does not match the second plurality of metadata; and cause the identified metadata to be included in the one of the first catalog or the second catalog.

19. The video provisioning system of claim 18, wherein the server device includes a video content management server that ingests video assets from content providers of video assets and provides metadata associated with the video assets to at least one of the first catalog or the second catalog.

20. The video provisioning system of claim 18, wherein the identified metadata includes one or more of:

a description of a particular video asset;

a price structure associated with the particular video asset;

bundle information associated with the particular video asset;

information about a storage location of the particular video asset;

information regarding an availability of the particular video asset;

information about digital rights management associated with the particular video asset;

cover art associated with the particular video asset; a rating associated with the particular video asset; or a review associated with the particular video asset.

21. The video provisioning system of claim 18, wherein the first and second plurality of metadata comprises information stored in multiple fields of a video asset record, and wherein, when determining whether the first plurality of metadata matches the second plurality of metadata, the server device is further configured to:

select fewer than all of the multiple fields; and perform a comparison of the first plurality of metadata to the second plurality of metadata using information stored in the selected fewer than all of the multiple fields.

22. A non-transitory storage medium storing computer-executable instructions that, when executed, cause one or more processors of a server device to:

receive user input indicating that a video asset that is published in a first catalog of video assets corresponding to a first type of video format, is not published in a second catalog of video assets corresponding to a second type of video format, execute, based on the user input, one or more instructions to synchronize the first and second catalogs of video assets;

obtain a first plurality of metadata, associated with the one or more video assets, from a first device that includes the first catalog of video assets, wherein the first catalog is accessible through a set top box;

obtain a second plurality of metadata, associated with one or more video assets, from a second device that includes the second catalog of video assets, wherein the second catalog is accessible through a device other than a set top box;

determine whether the first plurality of metadata matches the second plurality of metadata;

identify metadata that is not included in one of the first catalog or in the second catalog, when the first plurality of metadata does not match the second plurality of metadata; and cause the identified metadata to be included in the one of the first catalog or the second catalog.

23. The non-transitory storage medium of claim 22, wherein the server device includes a video content management server that ingests video assets from content providers of video assets and provides metadata associated with the video assets to at least one of the first catalog or the second catalog.

24. The non-transitory storage medium of claim 22, wherein the identified metadata includes one or more of:

a description of a particular video asset;

a price structure associated with the particular video asset;

bundle information associated with the particular video asset;

information about a storage location of the particular video asset;

information regarding an availability of the particular video asset;

information about digital rights management associated with the particular video asset;

cover art associated with the particular video asset; a rating associated with the particular video asset; or a review associated with the particular video asset.

25. The non-transitory storage medium of claim 22, wherein the first and second plurality of metadata comprises information stored in multiple fields of a video asset record, and wherein, when determining whether the first plurality of metadata matches the second plurality of metadata, the instructions further cause the one or more processors to:

select fewer than all of the multiple fields; and perform a comparison of the first plurality of metadata to the second plurality of metadata using information stored in the selected fewer than all of the multiple fields.

* * * * *